(12) United States Patent
Berkowitz et al.

(10) Patent No.: US 11,395,907 B2
(45) Date of Patent: *Jul. 26, 2022

(54) EXPANDABLE TISSUE DILATOR FOR DILATING TISSUE AROUND A SPINAL COLUMN

(71) Applicant: GLOBUS MEDICAL, INC., Audubon, PA (US)

(72) Inventors: Andrew Berkowitz, Philadelphia, PA (US); Brian Flint, Eagleville, PA (US)

(73) Assignee: Globus Medical, Inc., Audubon, PA (US)

( * ) Notice: Subject to any disclaimer, the term of this patent is extended or adjusted under 35 U.S.C. 154(b) by 490 days.

This patent is subject to a terminal disclaimer.

(21) Appl. No.: 16/456,615

(22) Filed: Jun. 28, 2019

(65) Prior Publication Data

US 2019/0381293 A1 Dec. 19, 2019

Related U.S. Application Data

(63) Continuation of application No. 15/269,081, filed on Sep. 19, 2016, now Pat. No. 10,369,338, which is a continuation-in-part of application No. 15/050,547, filed on Feb. 23, 2016, now Pat. No. 10,369,336.

(51) Int. Cl.
*A61M 29/02* (2006.01)
*A61B 17/34* (2006.01)

(52) U.S. Cl.
CPC ......... *A61M 29/02* (2013.01); *A61B 17/3421* (2013.01); *A61M 2210/1003* (2013.01)

(58) Field of Classification Search
CPC .............. A61B 17/3421; A61B 5/6853; A61B 2017/3486; A61M 29/02; A61M 2025/09008; A61M 2025/1056; A61M 25/10; A61M 25/1006
See application file for complete search history.

(56) References Cited

U.S. PATENT DOCUMENTS

| | | | |
|---|---|---|---|
| 5,035,694 A * | 7/1991 | Kasprzyk | A61B 18/082 606/27 |
| 5,370,134 A | 12/1994 | Chin et al. | |
| 5,575,815 A * | 11/1996 | Slepian | A61L 31/145 600/36 |
| 6,267,754 B1 * | 7/2001 | Peters | A61M 39/1011 604/533 |
| 6,537,247 B2 | 3/2003 | Shannon | |
| 6,564,078 B1 | 5/2003 | Marino et al. | |
| 6,623,451 B2 | 9/2003 | Vigil | |
| 7,079,883 B2 | 7/2006 | Marino et al. | |
| 7,892,275 B2 | 2/2011 | Hartley et al. | |
| 8,038,598 B2 | 10/2011 | Khachi | |
| 8,265,744 B2 | 9/2012 | Gharib et al. | |
| 8,489,170 B2 | 7/2013 | Marino et al. | |
| 8,597,240 B2 | 12/2013 | Davies et al. | |

(Continued)

*Primary Examiner* — Jocelin C Tanner

(57) ABSTRACT

An expandable tissue dilator for dilating tissue around a spinal column includes a housing and a shaft at least partially positioned distally of the housing and adapted to pierce a tissue around the spinal column. An expandable member attached to the housing expands around a portion of the shaft to dilate the pierced tissue in a single-pass dilation resulting in a reduction of any traumatic impingement of nerves or muscle tissue and reduction in procedure time.

18 Claims, 11 Drawing Sheets

(56) References Cited

U.S. PATENT DOCUMENTS

| | | | |
|---|---|---|---|
| 8,668,654 B1* | 3/2014 | Gerrans | A61B 5/1459 600/562 |
| 9,014,776 B2 | 4/2015 | Marino et al. | |
| 9,028,444 B2 | 5/2015 | Campbell et al. | |
| 9,226,772 B2* | 1/2016 | Fox | A61B 17/3478 |
| 10,369,338 B2* | 8/2019 | Berkowitz | A61B 17/3421 |
| 2003/0191435 A1* | 10/2003 | Shkolnik | A61M 25/1034 604/103 |
| 2004/0102701 A1* | 5/2004 | Nix | A61F 2/958 600/437 |
| 2010/0234838 A1* | 9/2010 | Watson | A61M 25/01 606/21 |
| 2012/0271339 A1* | 10/2012 | O'Beirne | A61M 25/104 606/194 |
| 2014/0018732 A1* | 1/2014 | Bagaoisan | A61M 25/0136 604/95.04 |

* cited by examiner

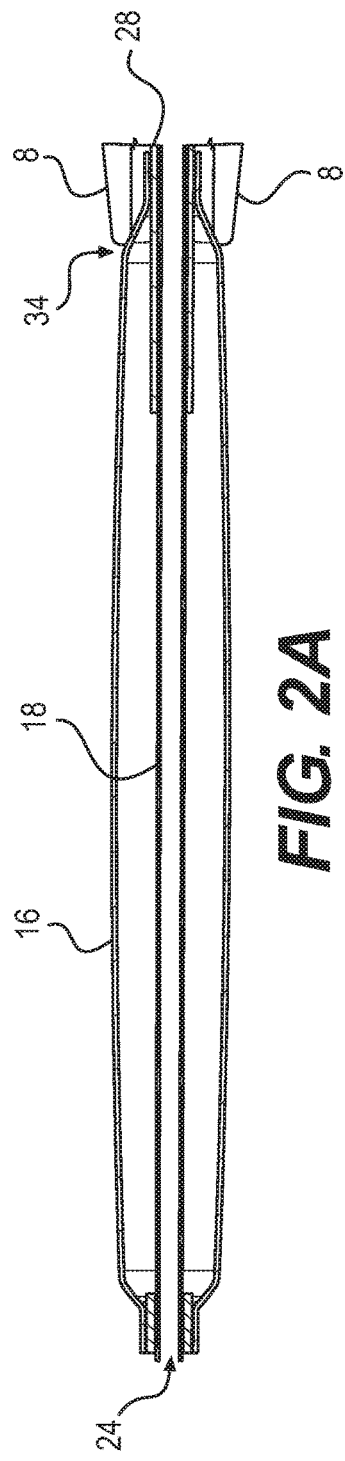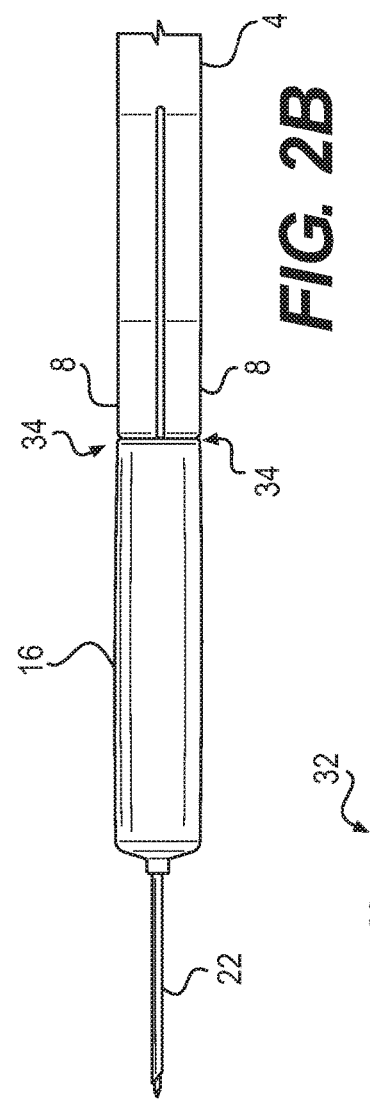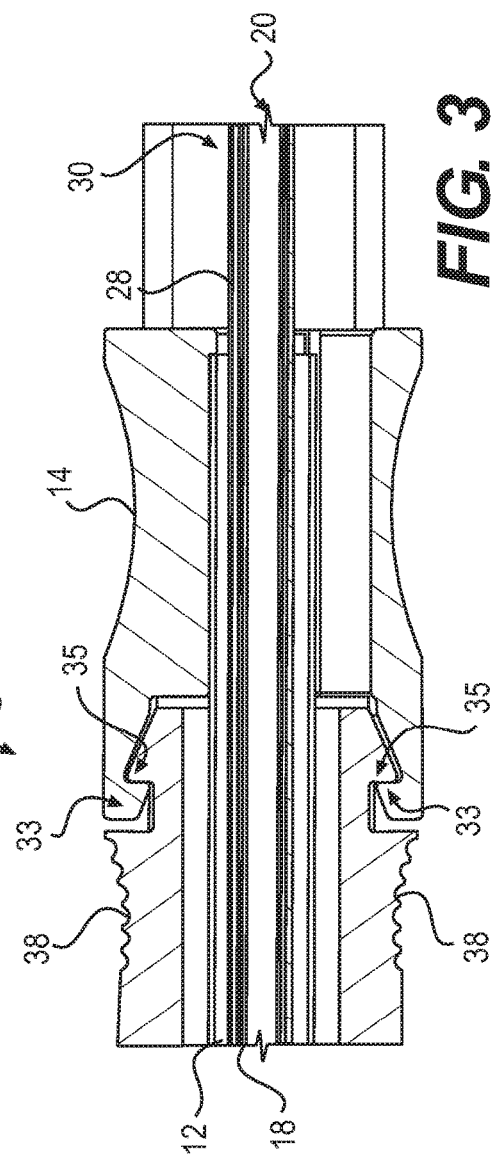

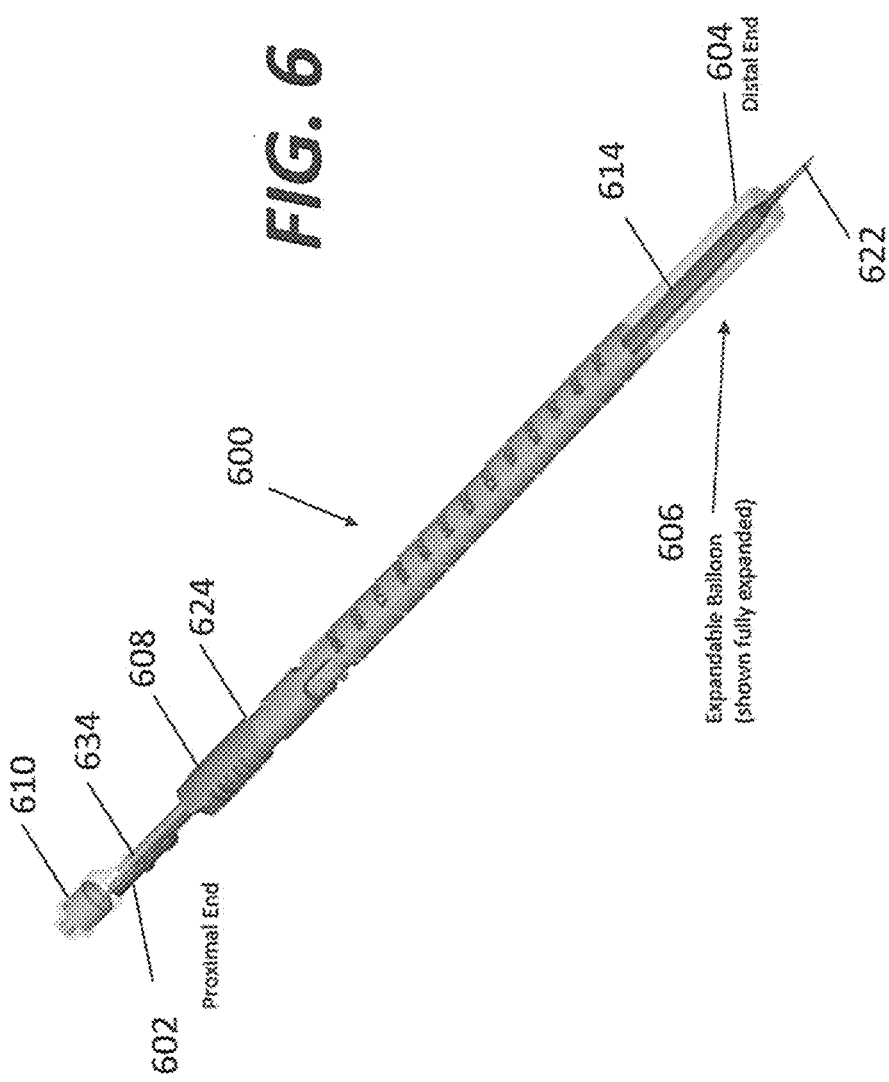

US 11,395,907 B2

EXPANDABLE TISSUE DILATOR FOR DILATING TISSUE AROUND A SPINAL COLUMN

CROSS-REFERENCE TO RELATED APPLICATION

The present application is a continuation application of U.S. patent application Ser. No. 15/269,081 filed Sep. 19, 2016 (published as U.S. Pat. Pub. No. 2017-0239452), which is a continuation-in-part of U.S. patent application Ser. No. 15/050,547 filed Feb. 23, 2016 (published as U.S. Pat. Pub. 2017-0239451), all of which are hereby incorporated by reference in their entireties.

FIELD

The present invention relates to a surgical apparatus, and more particularly to a dilator for dilating tissue around a surgical site.

BACKGROUND

The development of minimally invasive percutaneous procedures has yielded a major improvement in reducing recovery time and post-operative pain because minimal dissection of tissue (such as the psoas muscle tissue, for example) is needed. Minimally invasive surgical techniques are desirable for spinal and neurosurgical applications because of the need for access to locations within the body, and the danger of damage to vital intervening tissues and nerves.

Surgical procedures within the body, especially near the spine, require a set of dilators and a retractor to clear the tissue surrounding the spine before the spine can be accessed. An access procedure for a surgical operation begins with the insertion of a guide wire followed by a series of successively larger dilators installed in sequence to dilate the soft tissues such as the psoas muscle surrounding the spine. Then, following installation of the largest dilator deemed necessary, a retractor is advanced over the largest dilator for providing a working channel from the skin of the patient to working space adjacent the spine.

However, the set of conventional blunt dilators as described above has the potential to sever muscle fibers and irritate or otherwise disrupt the nerve roots which innervate the muscle tissue. This is especially true for dilating psoas muscle tissue to obtain access to the intervertebral disc space when performing a lumbar interbody fusion from a lateral approach.

Therefore, there is a need to provide an improved dilator and method for dilating the tissue with less muscle trauma and less damage to the nerve roots.

SUMMARY OF THE DISCLOSURE

An expandable tissue dilator for dilating tissue around a spinal column is provided. The dilator includes a housing and a shaft at least partially positioned distally of the housing and sufficiently stiff to pierce a tissue around the spinal column. An expandable member attached to the housing is expandable around a portion of the shaft to dilate the pierced tissue.

Advantageously, the expandable member of the dilator allows a single-pass dilation to occur instead of the conventional multi-pass dilation using multiple dilators. The single pass dilation reduces the likelihood of any traumatic impingement of nerves or muscle tissue and also reduces procedure time.

BRIEF DESCRIPTION OF THE DRAWINGS

FIG. 2A is a cross-sectional view of a distal portion of the expandable dilator of FIG. 1.

FIG. 2B is a side view of a distal portion of the dilator of FIG. 1 which has been expanded.

FIG. 3 is a cross-sectional view of a sliding switch of the dilator of FIG. 1.

FIG. 6 is a perspective view of an expandable dilator consistent with the present disclosure.

DETAILED DESCRIPTION

Figure 1:
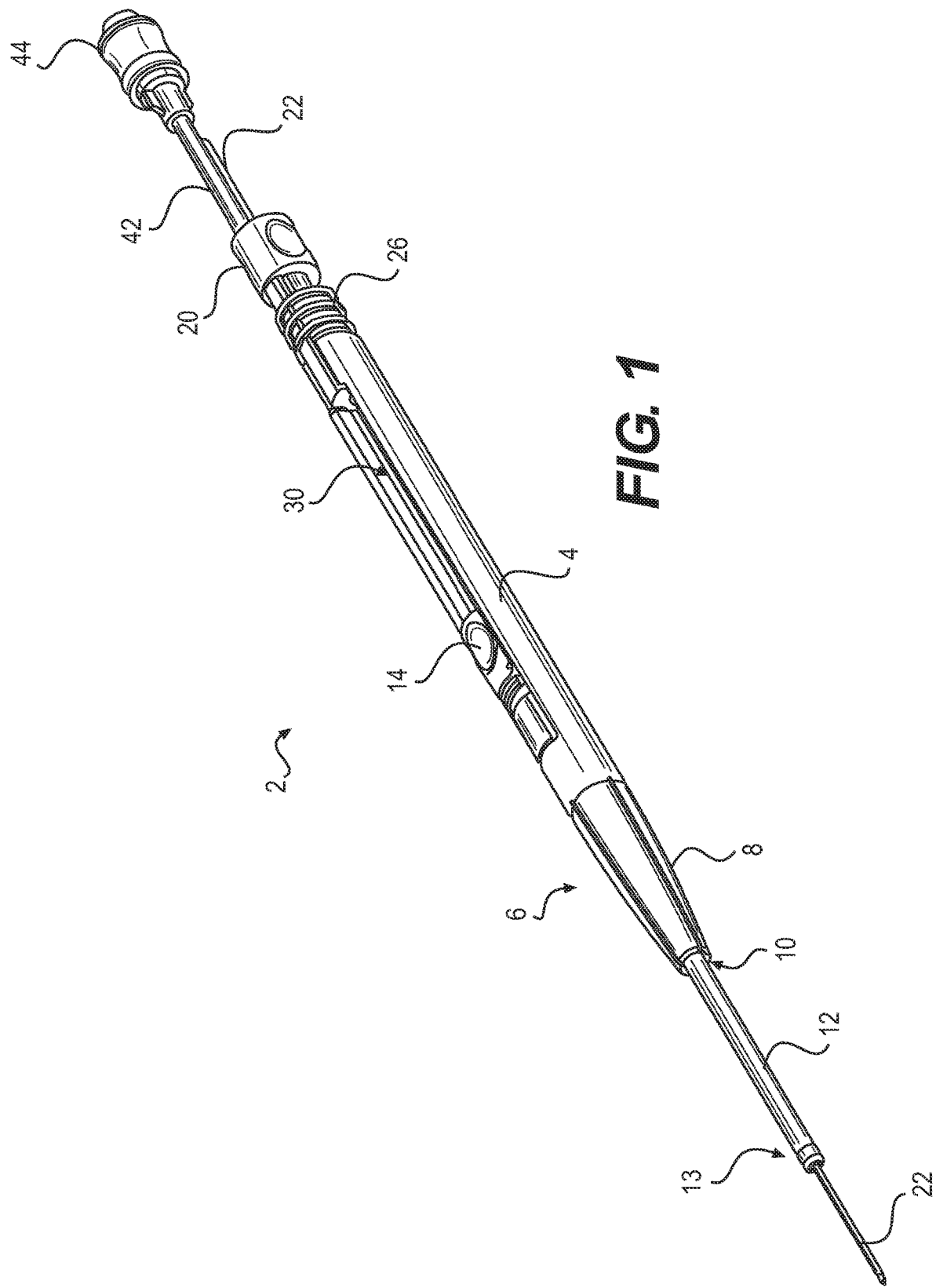
FIG. 1 is a perspective view of an expandable dilator consistent with the present disclosure.

FIG. 1 is a perspective view of a dilator according to an embodiment of the present disclosure. The dilator 2 includes a housing 4 having a tapered tip section 6. The tip section 6 is preferably shaped as a partial cone and includes a plurality of circumferentially and uniformly spaced tapered flaps 8 whose distal ends define an end opening 10. In the embodiment shown, there are four uniformly spaced tapered flaps 8. However, any number of flaps are acceptable. The housing 4 including the tip section 6 can be made of plastic material such as ABS plastic.

An outer shaft such as a sheath 12 extends through the opening 10 of the housing 4 and its proximal end terminates at a sliding switch 14. The sheath 12 is sufficiently strong and rigid to pierce any muscle tissue such as psoas muscle that surrounds the vertebral column. The outer sheath 12 can be made of stainless steel, for example.

The outer sheath 12 can be in an extended state to surround an expandable member 16 and a retracted state to expose the expandable member 16 for expansion against the muscle tissue. The outer sheath 12 is retractable by sliding the sliding switch 14 in the proximal direction. The retraction of the sheath 12 exposes the expandable member 16 such as a balloon (see FIG. 2A). Although the expandable member 16 is being referred to as a balloon 16, it is contemplated that expandable member 16 may be any structure capable of expanding. Referring to FIG. 2A, the balloon 16 is attached around an outer surface of an inner shaft such as an inner sheath 18 and is in fluid communication with an inflation lumen 28 that surrounds the inner sheath 18. The inner sheath 18 and the inflation lumen 28 extend through the housing 4 and terminate at a hub 20 which is attached to a proximal end of the housing 4. As shown, the balloon 16 is approximately 60 mm in length but other lengths are contemplated including lengths from 5 mm to 180 mm.

A tubing 42, in fluid communication with the inflation lumen 28, extends between the hub 20 and a luer connector 44. In operation, an inflation fluid source such as a fluid filled syringe (not shown) is connected to the connector 44 and provides the fluid for inflating the balloon 16.

The preferred inflation fluid depends on the type of imaging modality. When fluoroscopic imaging is used, an Iodine based contrast media or Gadolinium based contrast media can be used for improved visibility. Otherwise, saline solution or even water can be acceptable.

In the embodiment shown, the inner sheath 18 has a through-hole 24 for accommodating a guidewire 22 which is inserted through the through-hole 24 from the proximal end of the inner sheath. The distal end of the inserted guidewire 22 is inserted into a soft disc material within a vertebral column during the insertion and operation of the dilator 2. This facilitates docking of the dilator 2 with respect to the operative level to prevent inadvertent movement of the dilator 2.

The inner sheath 18 can be made of a single stainless steel tube, a steel coil reinforced TPU tube, or a steel reinforcing braid laminated between two TPU tube layers. Among others, the tube reinforcements serve two purposes. The first is to prevent occlusion of the inner lumen 18 when the balloon 16 is inflated to allow for positioning of the guidewire 22 at any time throughout the procedure. The second is the reinforced or rigid steel tubing prevents axial growth of the balloon 16 when under pressure, so that expansion occurs generally radially.

An occlusion switch 26 slides along a distal portion of the hub 20 to seal an inflation lumen 28 (see FIG. 2A) once the balloon 16 has been inflated with the fluid as will be explained in more detail later herein.

As can be appreciated, the present invention provides several advantages over existing devices and methods for providing access to the intervertebral disc space. Using an expandable balloon to dilate the psoas muscle allows for a single-pass dilation to occur. This reduces the probability of any traumatic impingement of nerves or psoas muscle tissue during the initial insertion of the device. Also, by expanding the psoas muscle fibers from within (i.e., by expansion of the expandable member 16), the muscle fibers are more likely to be pushed aside, rather than punctured or severed. Additionally, due to the smooth transition point 34 at the distal end of the housing 4, the present invention is less susceptible to tissue creep whereas, in conventional systems, clearances were present between the sequential dilators. Furthermore, the present invention includes a single instrument that would take the place of several dilators. As a result, the present invention allows a reduction in procedural steps and consequently operative time.

Referring to FIG. 2A, the balloon 16 is a semi-compliant thermoplastic polyurethane (TPU) balloon which is in a partially expanded state. Prior to expansion, the balloon 16 is folded over the inner sheath 18 and enclosed within the outer sheath 12. As shown, the outer sheath 12 is a stainless steel sheath. The sheath 12 provides the necessary rigidity for dissection through soft tissue and muscle to the intervertebral disc.

The sheath 12 is coated with an electrically insulating layer, except at the distal end and proximal end. At the distal end, the insulating layer has been stripped from a small area 13 of between 1 and 3 mm in width such that it is electrically conductive. During insertion of the dilator 2, the conductive distal area 13 contacts the tissue as it is being dissected. The proximal end (electrically conductive portion) of the sheath 12 can be connected to a diagnostic device (not shown) to monitor any unusual electrical activity at the conductive area 13 in contact with the tissue which may indicate problems such as a pressed nerve.

As shown in FIG. 2A, the balloon 16 has an inclined tapered portion at the proximal and distal ends. The distal ends of the flaps 8 of the tip section 6 are positioned to rest on the proximal portion of the balloon 16 and preferably on the inclined tapered proximal portion of the balloon. In its fully expanded state, the outer diameter of the balloon 16 closely matches that of the housing 4 (see FIG. 2B). As shown more clearly in FIG. 2B, as the balloon 16 expands, the flaps 8 resting on the balloon 16 also stretch and radially to provide a smooth transition point 34 and smooth surface along the length of the dilator 2 for a smooth insertion of a retractor over the dilator and minimal tissue creep. Preferably, the balloon 16 is either a semi-compliant or fully compliant balloon since the diameter of a fully expanded balloon is relatively definite.

As the expanding balloon applies substantial pressure against the inner sheath 18, the sheath is rated for (rated to withstand) at least 100 psi, and preferably at least 300 psi.

FIG. 3 is a cross-sectional view of a sliding switch of the dilator of FIG. 1. The sliding switch 14 is attached to the outer surface of the outer sheath 12. The switch 14 is slidably received in a longitudinal recess 30 of the housing 4. When the switch 14 longitudinally slides along the recess 30 in a proximal direction, the outer sheath 12 is retracted to expose an uninflated balloon 16. Conversely, when the switch 14 slides in a distal direction, the outer sheath 12 slides over and covers the balloon 16 so that the balloon is protected when the dilator 2 is not being used. When the sliding switch 14 slides towards the distal end of the recess 30, a locking mechanism 32 locks the switch to the housing 4 to ensure that the outer sheath 12 covers and protects the uninflated balloon 16.

The locking mechanism 32 includes a pair of protrusions 33 extending radially inwardly from the switch 14 and a pair of hooks 35. The protrusion 33 extends radially inwardly while the hook 35 extends radially outwardly to mate with the protrusion to lock the sliding switch 14. The locking mechanism 32 further includes a pair of release buttons 38 attached to the housing 4 and coupled to the respective hooks 35. The release button 38 is biased away from the longitudinal axis of the housing 4 such that depression of the release button moves the hooks 35 radially inwardly and unlocks the sliding switch 14 from the housing 4.

Figure 4A:
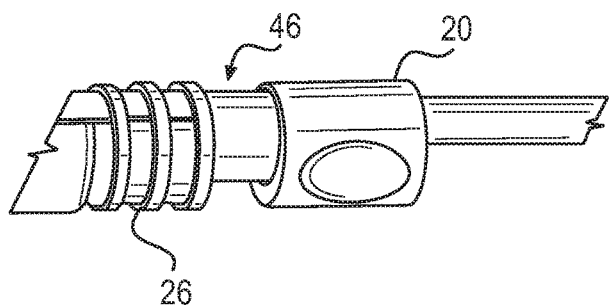
FIG. 4A is a perspective view of a sealing switch and hub of the dilator of FIG. 1.
Figure 4B:
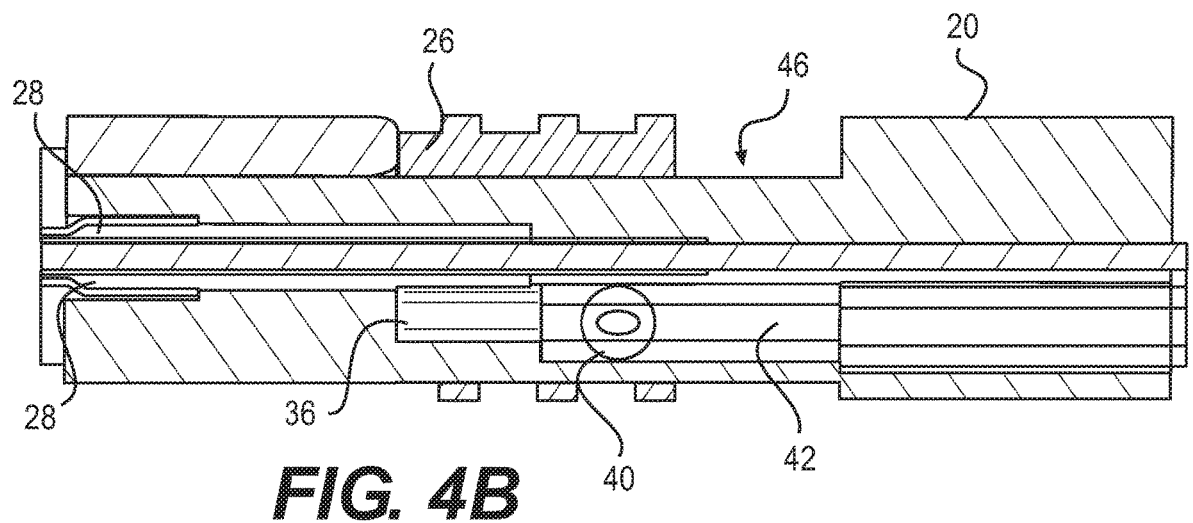
FIG. 4B is a cross-sectional view of the sealing switch and hub of the dilator of FIG. 1.
Figure 4C:
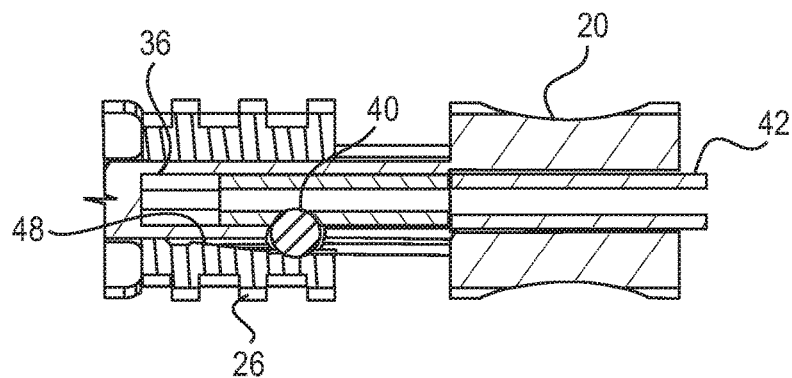
FIG. 4C is another cross-sectional view of the sealing switch and hub of the dilator of FIG. 1, which is rotated 90 degrees from that of FIG. 4B.

FIG. 4A is a perspective view of an occlusion switch 26 and hub 20 of the dilator of FIG. 1. A portion of a narrow distal portion 46 of the hub 20 is inserted into the proximal end of the housing 4 and is permanently affixed thereto with an adhesive. The occlusion switch 26 slides along the narrow distal portion 46 of the hub 20 to open and seal the inflation lumen 28 (see FIGS. 4B and 4C).

The hub contains a chamber 36 in fluid communication with the inflation lumen 28. A tubing 42 is in fluid communication with the chamber 36. An occluding ball 40 is positioned inside a lateral recess (not shown) and over the tubing 42. An inclined inner surface (ramp) 48 of the occlusion switch 26 is in contact with the occluding ball 40. When the occlusion switch 26 is moved proximally along the narrow portion 46, the inclined surface 48 presses the ball 40 radially inwardly which results in occluding the tubing 42. Since the tubing 42 is in communication with the inflation lumen 28 through the chamber 36, the proximal movement of the occlusion switch 20 seals the inflation lumen 28 from the inflation fluid source connected to the tubing 42. In effect, the inflation lumen, chamber 36 and tubing 42 are all a part of an inflation channel, and the occluding ball 40 can be positioned anywhere along the inflation channel.

With the outer sheath 12 retracted by the sliding switch 14, the balloon 16 is filled and pressurized with an inflation fluid which stretches the balloon and provides the necessary radial force to dilate the psoas muscle, while allowing for visualization under intra-operative fluoroscopic imaging. As the balloon 16 is expanded, the distal ends of the flaps 8 of the dilator 2 resting on the inclined surface of the balloon 16 will splay apart, maintaining a continuous outer surface free of any corners or edges. The distal ends of the flaps are also radiused to provide a smooth transition between the flaps and the expandable balloon. These features allow a retractor (not shown) to be smoothly introduced over the dilator 2.

When the balloon 16 is fully expanded, the occlusion switch 26 acts as a stopcock, maintaining pressure within the balloon and allowing the inflation device to be disconnected. In a spinal surgery, disconnecting the inflation device is necessary to allow for insertion of a retractor over the dilator 2.

A method of dilating the tissue will now be explained. First, a physician would make an incision of skin. Second, the dilator 2 is inserted through the incision and is slowly pushed through the muscle tissue while electrical activity from the electrically conductive tip 13 of the outer sheath 12 is monitored for any unusual activity. During the insertion step, the physician may need to reposition the dilator 2 depending on the electrical activity readings from the diagnostic device.

Third, a guidewire 22 is inserted through the through-hole 24 of the inner sheath 18 and its tip is inserted into the soft intervertebral disc space. Fourth, the outer sheath 12 is retracted to expose an uninflated balloon 16 by first depressing the release buttons 38 to release the lock, and then sliding the sliding switch 14 proximally while holding the housing 4 steady. Fifth, attach an inflation device such as a syringe to the connector 44 and inject an inflation fluid through the inflation lumen 28 to inflate the balloon 16. The expansion of the balloon 16 dilates the muscle tissue in contact with the dilator 2. Sixth, once the balloon 16 is inflated to a desired level or pressure, the inflation lumen 28 is occluded by using the occlusion switch 26. Seventh, a retractor is slid over the dilator 2 and expanded balloon 16. Eighth, the inserted retractor is then used to further dilate the muscle tissue to create a working channel into the surgical site.

Figure 5A:
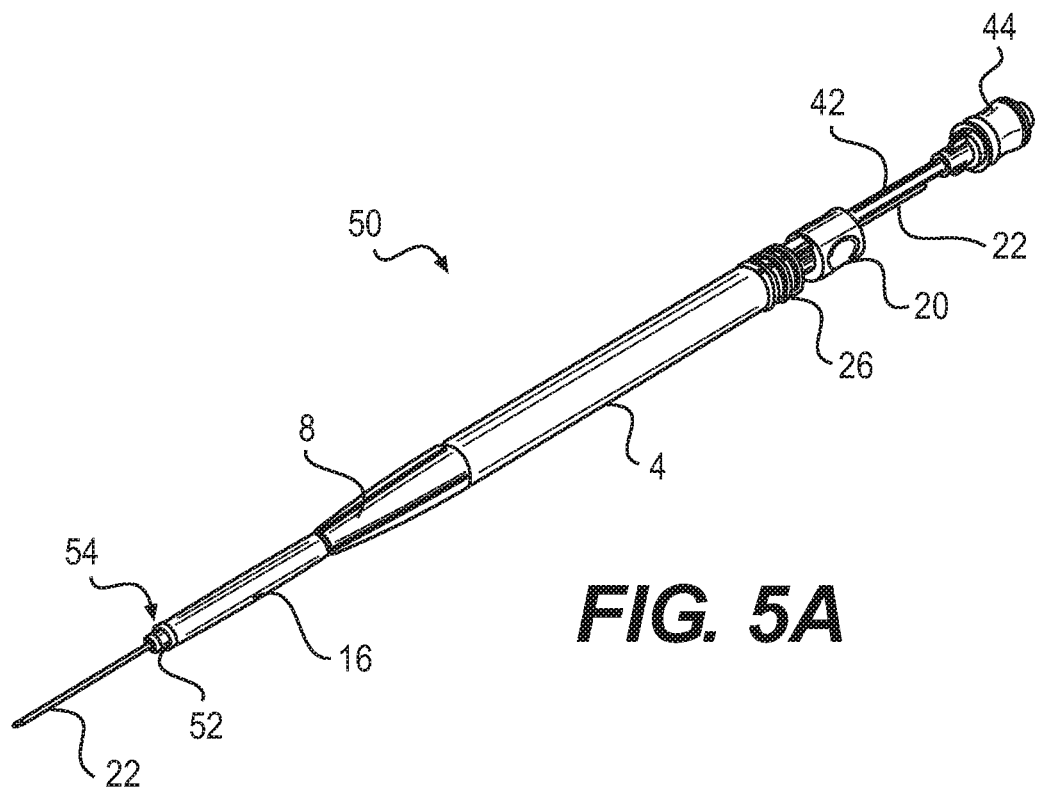
FIG. 5A is a perspective view of an expandable dilator consistent with the present disclosure.
Figure 5B:
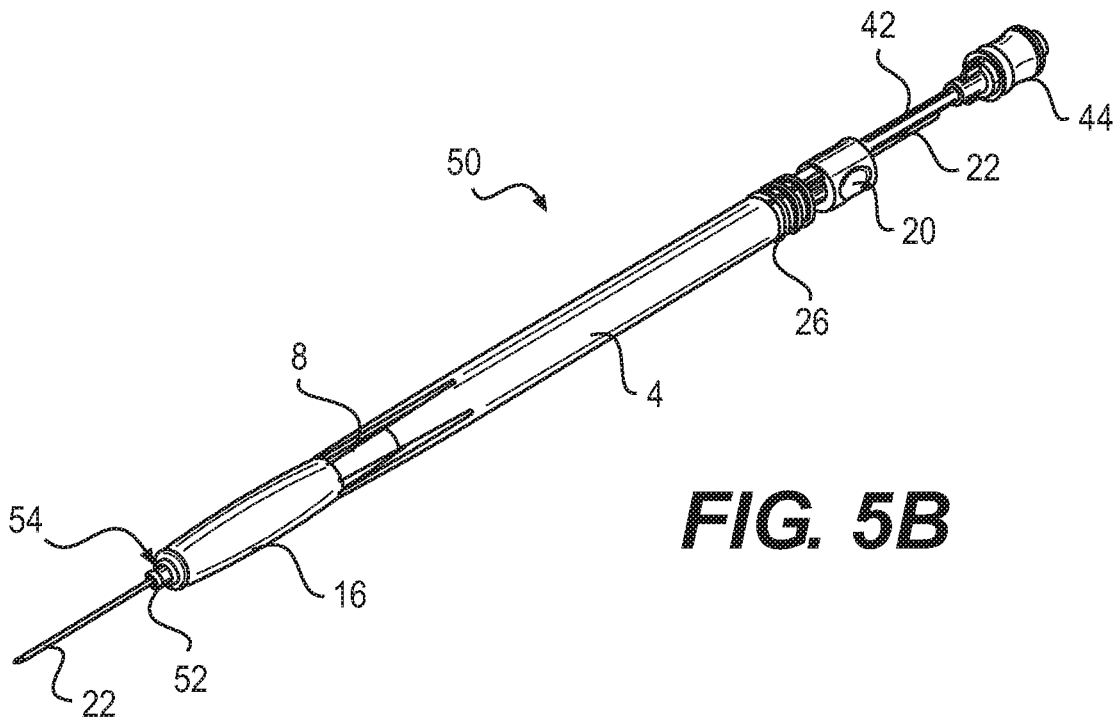
FIG. 5B is a perspective view of the dilator of FIG. 5A which has been expanded.

FIGS. 5A and 5B illustrate an expandable dilator according another aspect of the present invention. Unlike the dilator of FIG. 1, the dilator 50 does not have an outer sheath 12. An inner sheath/tube 52 to which the balloon 16 is attached is a slightly larger diameter and thicker sheath than the inner sheath 12 of FIG. 1. The inner sheath 52 is made of stainless steel, for example. The additional rigidity provided by the larger and thicker inner sheath 52 eliminates the need for an outer sheath 12. This simplified design does not require a sliding switch and therefore reduces the number of procedural steps. In the absence of an outer sheath 12, the inner tube 52 is coated in an insulating layer throughout its length, except the distal end which has a small conductive outer surface 54 and proximal end which also has a conductive area for connection to a diagnostic device for monitoring electrical activity near the distal tip of the inner sheath 52.

FIG. 6 illustrates a dilator 600 consistent with the present disclosure. Dilator 600 may include a proximal end 602, distal end 604, balloon 606, switch 608, luer connector 610, and guidewire 622. Some of the aforementioned components may be the same or similar to components previously described herein.

Like dilators 2 and 50 explained above, expansion of dilator 600 may be achieved by means of balloon 606 disposed at distal end 604 of dilator 600. Balloon 606 may be inflated and pressurized in order to expand even when restricting anatomical structures in a patient are encountered.

Figure 7:
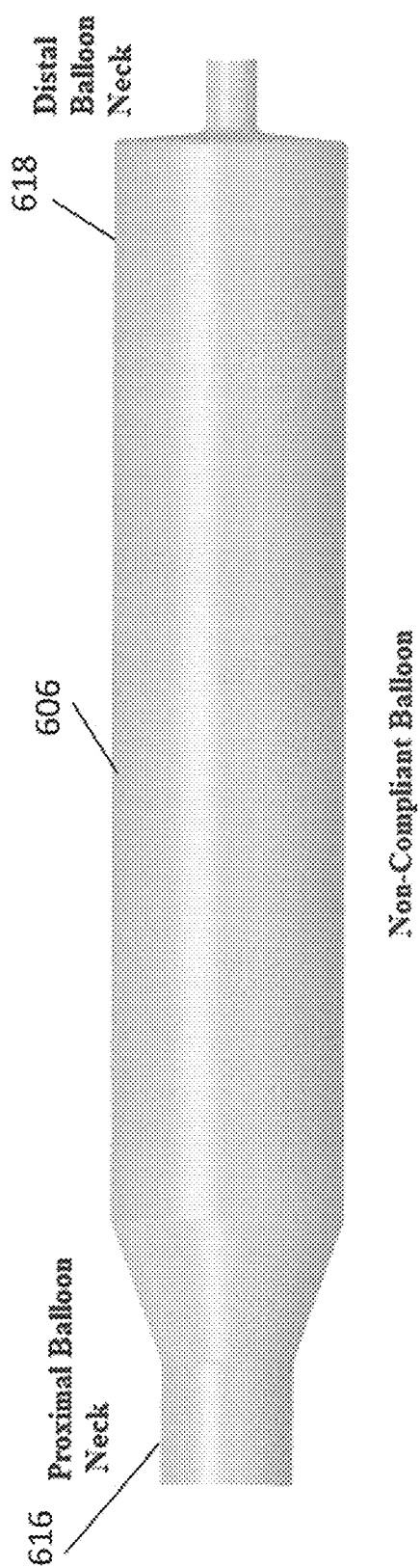
FIG. 7 is a perspective view of an expandable balloon used in the dilator of FIG. 6 consistent with the present disclosure.

Balloon 606 may be similar to those described herein. Balloon 606 may also be non-compliant and/or exhibit properties that limit its expansion beyond its preformed shape and dimensions. In an unexpanded state, balloon 606 may be folded in such a way that its profile is minimized to provide the greatest ratio of expanded to collapsed dimensions, allowing unimpeded insertion into a patient with balloon 606 in an unexpanded state. Balloon 606 may also provide that when pressurized, it may inflate to a defined and repeatable shape and size, which can be controlled and manipulated through manufacturing process parameters. Balloon 606 may be manufactured from thermoplastic polymers, such as nylon or PET (polyethylene terephthalate). Balloon 606 may have a repeatable inflated diameter which may provide additional compatibility with a tissue retractor which may be introduced after dilation is complete. As shown in FIGS. 6-7, balloon may have a squared-off geometry at its distal end which may aid in preventing invasion of tissue between the expanded tip of the balloon and the surgical site.

Figure 8:
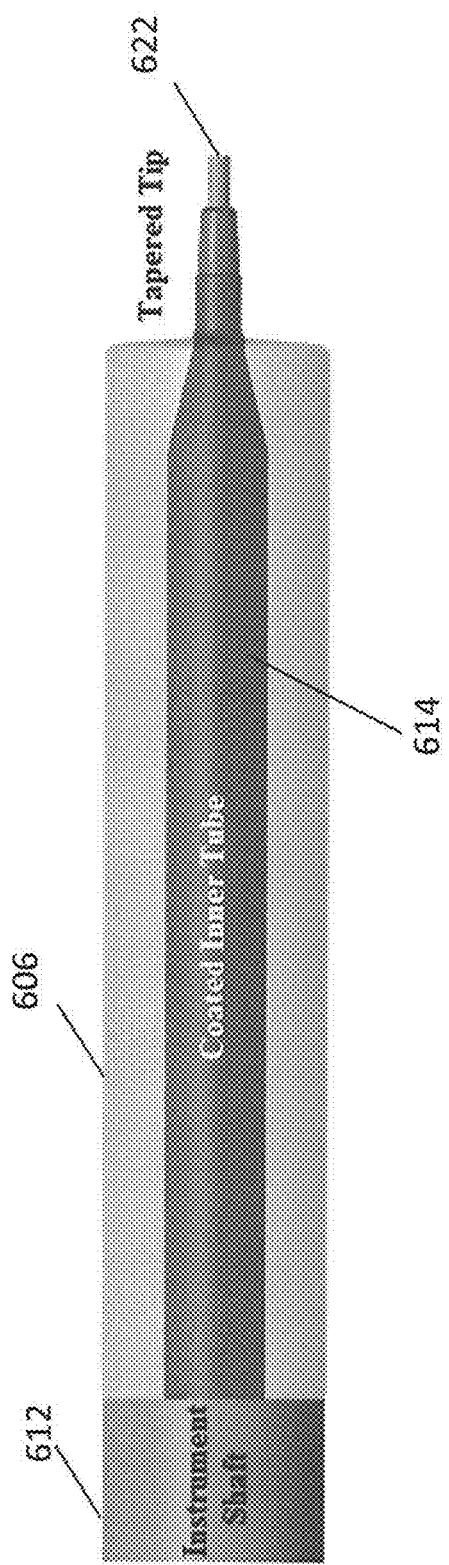
FIG. 8 is a cross-sectional view of a distal portion of the dilator of FIG. 6 consistent with the present disclosure.

As illustrated in FIG. 8, proximal to balloon 606, a shaft 612 of dilator 600 may be sized such that a diameter of dilator 600 is the same or similar with that of expanded balloon 606. An advantage of such a configuration is that it may provide a continuous outer surface over which the subsequently introduced retractor blades can slide, free of or with relatively minimal obstruction. Depth markings may be present along the exterior surface of dilator 600 which indicate the retractor blade length that is appropriate based on the patient's anatomy. The depth markings may be uniform and symmetric about the longitudinal axis of the device, such that the information conveyed by the marking is identical for any given patient and dilator positioning, regardless of the axial rotation of the device or viewing angle.

Along the longitudinal axis of dilator 600, an inner tube 614 may be attached to balloon 606 at or near distal end 604. Inner tube 614 may be made of a rigid material such as stainless steel which may provide sufficient flexural strength for initial dissection of soft tissue and instrument placement at the surgical site. Inner tube 614 may have a tapered, atraumatic tip geometry which may allow for smooth insertion of the instrument when balloon 606 is in a collapsed state, and may reduce the likelihood of inadvertent impingement of anatomical structures such as nerve roots. Cannulation of inner tube 614 may allow for placement of guidewire 622 through the longitudinal axis of the instrument.

Balloon 606 may contain proximal neck region 616 and distal neck region 618. At regions 616 and 618, the diameter of balloon 606 may be reduced and other components can be bonded or assembled. Distal neck region 618 of balloon 606 may be bonded to inner tube 614 such that a leak-proof seal is created. This bond may be achieved by reflowing, or melting, the balloon neck material to cause a weld between the inner tube 614 and distal neck region 618. Inner tube 614 may be surface-treated with a nylon or other thermoplastic coating to promote adhesion with balloon 606. Alternatively, a roughening treatment such as a bead blast could be used to promote adhesion by creating a porous surface to which the reflowed balloon neck can mechanically interlock. A medical grade adhesive would be an alternative method of bonding the balloon neck and inner tube.

Figure 9:
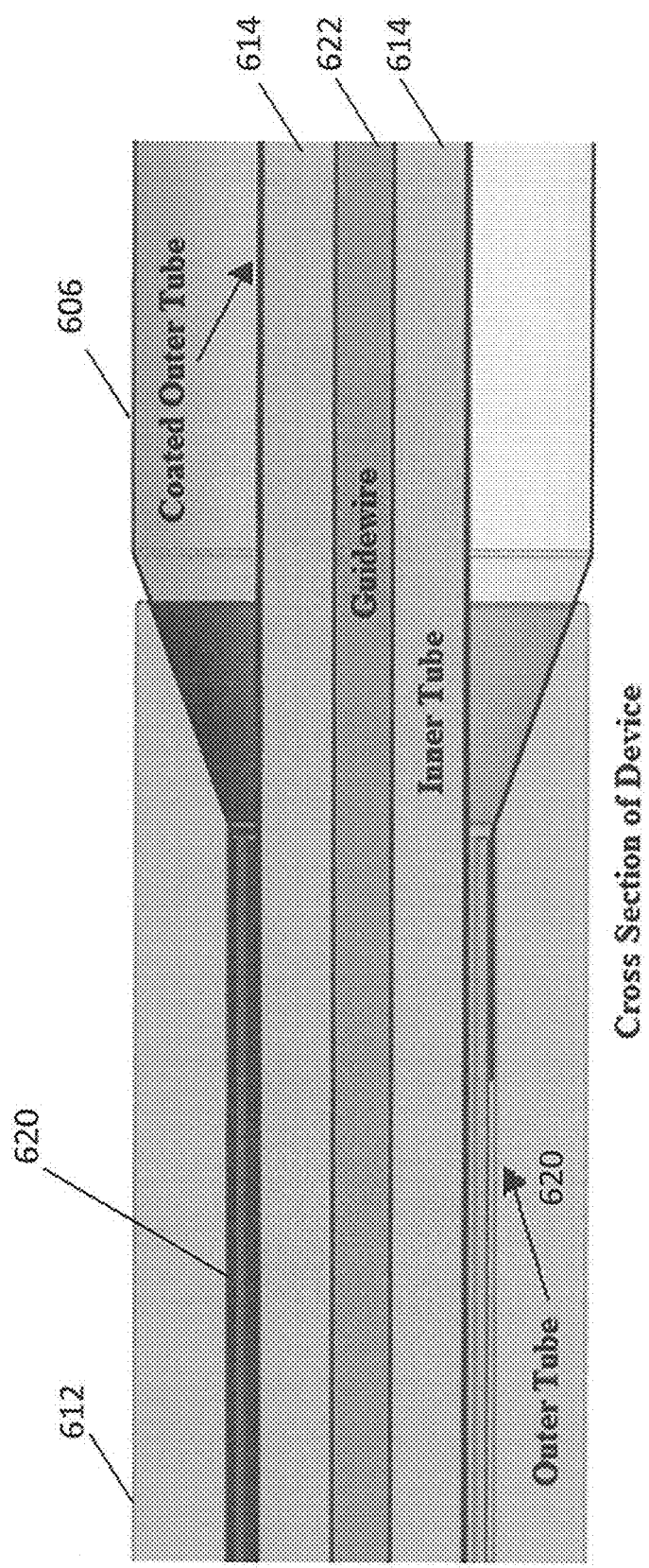
FIG. 9 is a cross-sectional view of distal portion of the dilator of FIG. 6 consistent with the present disclosure.

As illustrated in FIG. 9, an outer tube 620 of dilator 600 may be bonded to proximal neck region 616 of the balloon 606. This may close the enclosure of balloon 606 and allow it to pressurize without leaking when fluid is introduced into the enclosure to expand balloon 606. Outer tube 620 may be made of a thermoplastic material similar to that of balloon 606. This may allow a thermal bonding process to be used. A polymer such as nylon or a polyether block amide may be used for this application. As an alternative, an adhesive may be used for bonding this joint between outer tube 620 and balloon 606.

Inner tube 614 and outer tube 620 may extend through shaft 612 and terminate at a proximal hub 624. Inner tube 614 and outer tube 620 may be bonded into hub 624 with a medical grade adhesive which maintains a closed, leak-proof system. Balloon 606 may be inflated by injecting a mixture of saline and a radiopaque contrast medium through proximal hub 624 and into space 626 that is defined by a clearance between inner tube 614 and outer tube 620. Space 626 may extend to balloon 606 which facilitates expansion as a volumetric capacity of balloon 606 is approached.

Figure 10:
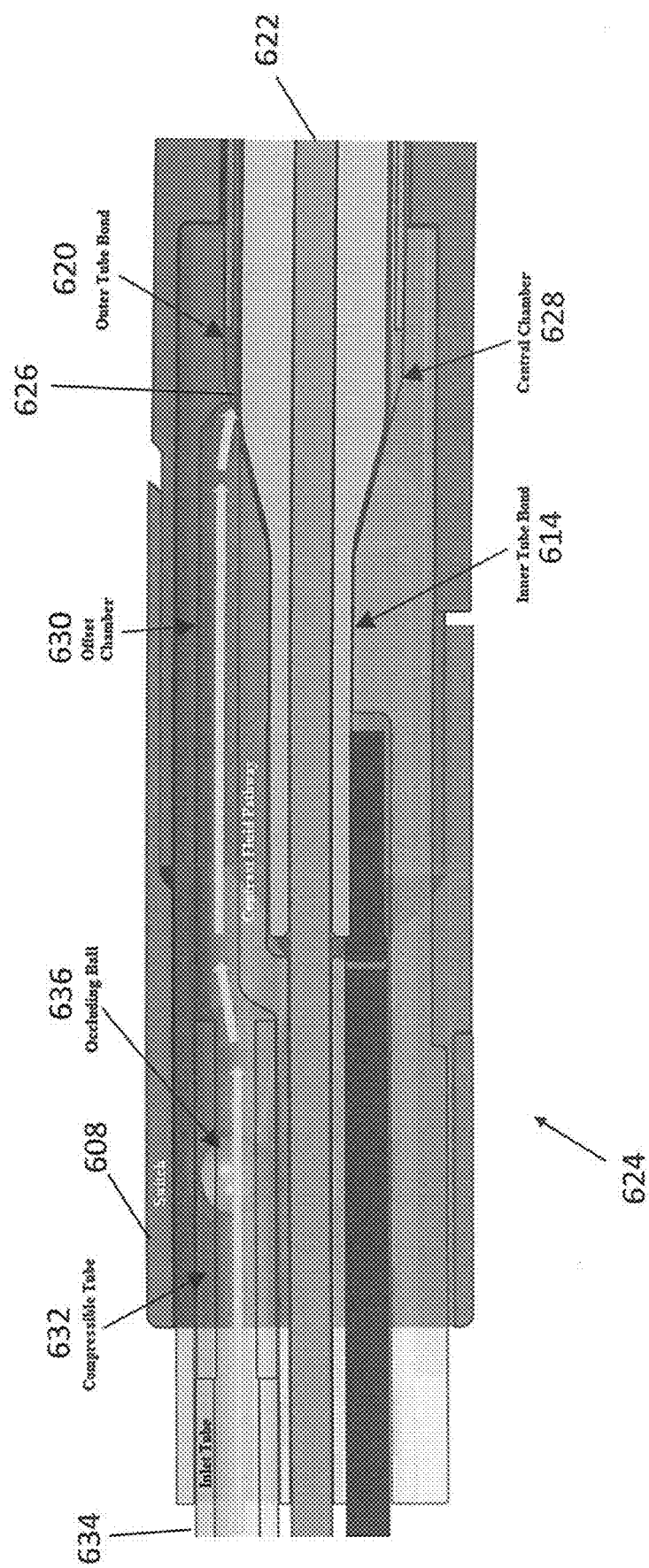
FIG. 10 is a cross-sectional view of proximal portion of the dilator of FIG. 6 consistent with the present disclosure.

With reference to FIG. 10, proximal hub 624 may include two chambers, central chamber 628 and offset chamber 630. Chambers 628 and 630 may intersect to allow fluid communication between them. Central chamber 628 may be the point where the inner tube 614 and outer tube 620 are bonded. Central chamber may surround guidewire 622. Offset chamber 630 may be positioned off-center from a longitudinal axis of dilator 600, such that it may intersect with a largest part of central chamber 628 without intersecting the path of guidewire 622.

Offset chamber 630 may provide an inlet for fluid, for example the contrast/saline mixture mentioned above, to be injected via an external inflation device. The fluid may be introduced through a tube 632, for example a flexible high-pressure tube, a reinforced polyurethane, nylon, or PVC material. Tube 632 may be bonded to a proximal end of offset chamber 630, for example using an adhesive. Tube 632 may terminate at its proximal end at a luer-activated valve such as luer connector 610. Luer connector 610 may be sealed when a male luer is not attached. Luer connector may be bonded to tube 632 via adhesive.

Dilator 600 may also include a sealing mechanism in addition to the sealing properties of luer connector 610. This additional sealing mechanism may further permit detachment of the external inflation device (not shown) while maintaining pressure within balloon 606. This may further facilitate retractor placement over dilator 600.

The sealing mechanism may include tube 632, which may be a soft, compressible internal tube present within offset chamber 630 in proximal hub 624. Tube 632 may be disposed such that it is in series with high pressure tube 634. In operation, injected fluid would travel through luer connector 610, then high pressure tube 634, and then tube 632 before intersecting with central chamber 628.

Tube 630 may be compressible and allows the fluid pathway to be occluded and sealed. Occulation may be accomplished by actuating a switch 608 on dilator 600, which moves a occulating ball 636 or dowel to press into tube 632 and compress it flat. Switch 608 may translate along a longitudinal axis of dilator 600 or rotate or clamp around tube 632.

Alternatively, a higher pressure sealing feature or device may be incorporated into high pressure tube 634, such that it either replaces or is in series with luer connector 610. This may be actuated in a similar manner, or in a rotational manner such as a stopcock.

Figure 11:
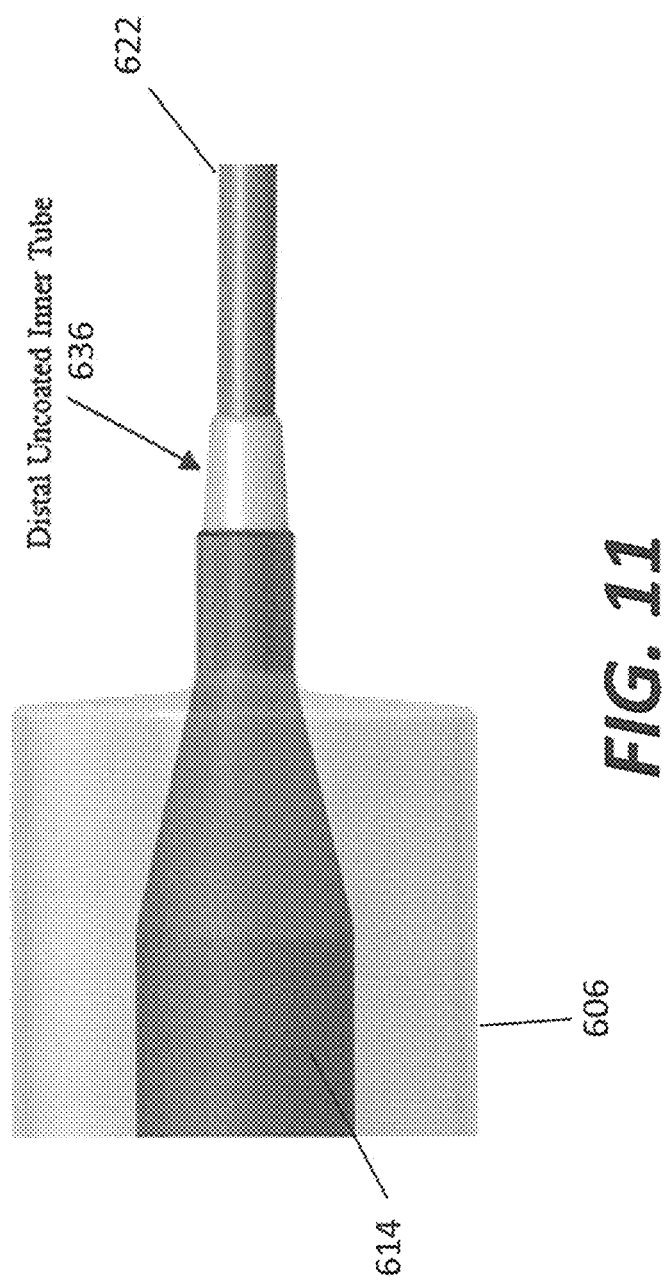
FIG. 11 is a cross-sectional view of distal portion of the dilator of FIG. 6 consistent with the present disclosure.
Figure 12:
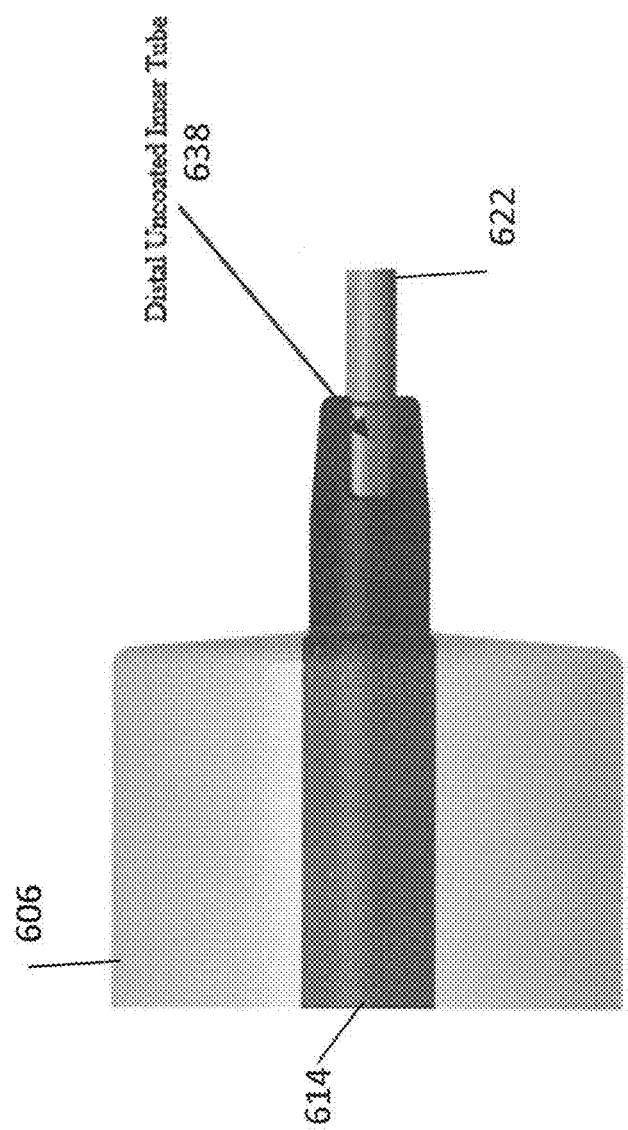
FIG. 12 is a cross-sectional view of distal portion of the dilator of FIG. 6 consistent with the present disclosure.

FIG. 11 illustrates distal end 604 of dilator 600. Distal end 604 may contain an uncoated region of inner tube 614 that is exposed through the end of dilator 600. The exposed end of dilator 600 may provide for neuromonitoring (t-EMG) where inner tube 614 may be used as an electrically conductive probe. Coating (for example nylon coating) to which balloon 606 is bonded at the distal tip extends along inner tube 614. This provides for inner tube 614 to be insulated thereby limiting the occurrence of shunting. The coating terminates along the length inner tube 614 leaving an un-coated area at each end, allowing current to pass through and be monitored via the device. The distal un-coated region 636 is exposed past the end of balloon 606, and is in contact with the patient's tissue during dissection/insertion of dilator 600. The proximal un-coated region is situated within proximal hub 624 and provides a means of attaching inner tube 614 to an external monitoring device. Alternatively, the exposed distal end of dilator 600 may only expose a portion 638 of the distal end of inner tube 614 as shown in FIG. 12.

One method of neuromonitoring may include attaching a wire which is exposed at the one end. The wire can be wrapped around or in contact with inner tube 614 at the one end, and which features a common connector for the monitoring equipment at the other end. Another method of contacting inner tube 614 would be to use a banana plug, spring clip, or other similar jack that could plug into or otherwise connect with the side or back of proximal hub 624 and contact the uncoated region of the inner tube.

It is to be understood that the disclosure describes a few embodiments and that many variations of the invention can easily be devised by those skilled in the art after reading this disclosure and that the scope of the present invention is to be determined by the following claims.

What is claimed is:

1. A method for dilating tissue of a patient using an expandable tissue dilator, said method comprising:
    making an incision on the patient;
    inserting the expandable tissue dilator through the tissue of the patient, wherein the expandable tissue dilator comprises:
        a shaft having a proximal end and a distal end;
        an expandable balloon disposed on the distal end of the shaft, the balloon having a proximal neck region and a distal neck region and wherein the expandable balloon is configured to expand to a predetermined shape and dimension upon receiving a fluid;

an inner tube disposed inside the shaft and attached to the expandable balloon at the distal neck region, wherein the inner tube is configured to receive a guidewire; and an outer tube that at least partially surrounds the inner tube whereby a space is disposed in between the outer tube and the inner tube and wherein the outer tube is attached to expandable balloon at the proximal neck region;

a hub including an off-set chamber, wherein the off-set chamber is completely disposed inside the hub off-center from a longitudinal axis of the dilator without intersecting the guidewire, wherein the expandable balloon is configured to receive the fluid via the space between the inner tube and the outer tube, inserting the guidewire through the expandable tissue dilator; and injecting fluid to inflate the expandable balloon.

2. The method of claim 1, wherein the expandable balloon is a non-compliant balloon.

3. The method of claim 1, wherein the hub is disposed at the proximal end of the shaft and configured to receive the inner tube and the outer tube.

4. The method of claim 3, wherein the hub comprises a central chamber, wherein the central chamber and the offset chamber intersect in order to allow fluid flow to the expandable balloon.

5. The method of claim 1, wherein the expandable balloon is configured to expand such that a diameter of the expandable balloon in an expanded position is substantially the same as a diameter of the shaft.

6. The method of claim 1, wherein the expandable balloon further comprises a luer connector configured to receive the fluid from an external inflation device, wherein the luer connector is further attached to the hub in to provide the fluid to the expandable balloon.

7. The method of claim 1, wherein the expandable balloon further comprises a switch that is configured to move between an open position and a closed position, wherein pressure within the expandable balloon is maintained when the switch is at the closed position.

8. The method of claim 7, wherein the switch is configured to move an occulating ball to press against a flexible tube within the hub to maintain pressure within the expandable balloon.

9. The method of claim 1, wherein the inner tube contains an insulated middle region, an uninsulated proximal region, and an uninsulated distal region, wherein the inner tube is further configured to provide neuromonitoring capabilities after insertion into a patient.

10. A method for dilating tissue of a patient using an expandable tissue dilator, said method comprising:
making an incision on the patient;
inserting the expandable tissue dilator through the tissue of the patient, wherein the expandable tissue dilator comprises:

a shaft having a proximal end and a distal end;

an expandable balloon disposed on the distal end of the shaft, the balloon having a proximal neck region and a distal neck region and wherein the expandable balloon is configured to expand to a predetermined shape and dimension upon receiving a fluid;

an inner tube disposed inside the shaft and attached to the expandable balloon at the distal neck region, wherein the inner tube is configured to receive a guidewire; and an outer tube attached to the expandable balloon at the proximal neck region, wherein the outer tube is disposed in a manner surrounding the inner tube and providing a space for receiving the fluid for expanding the expandable balloon;

a hub including an off-set chamber, wherein the off-set chamber is completely disposed inside the hub off-center from a longitudinal axis of the dilator without intersecting the guidewire, wherein the inner tube is comprised of an electrically conductive material and is configured to indicate the presence of a nerve as the expandable dilator traverses through soft tissue of a patient, inserting a guidewire through the expandable tissue dilator; and injecting fluid to inflate the expandable balloon.

11. The method of claim 10, wherein the expandable balloon is a non-compliant balloon.

12. The method of claim 10, wherein the hub is disposed at the proximal end of the shaft and configured to receive the inner tube and the outer tube.

13. The method of claim 12, wherein the expandable balloon further comprises a luer connector configured to receive the fluid from an external inflation device, wherein the luer connector is further attached to the hub in to provide the fluid to the expandable balloon.

14. The method of claim 12, wherein the hub comprises a central chamber, wherein the central chamber and the offset chamber intersect in order to allow fluid to flow to the expandable balloon.

15. The method of claim 10, wherein the expandable balloon is configured to expand such that a diameter of the expandable balloon in an expanded position is substantially the same as a diameter of the shaft.

16. The method of claim 10, further comprising a switch that is configured to move between an open position and a closed position, wherein pressure within the expandable balloon is maintained when the switch is at the closed position.

17. The method of claim 16, wherein the switch is configured to move an occulating ball to press against a flexible tube within the hub to maintain pressure within the expandable balloon.

18. The method of claim 10, wherein the inner tube contains an insulated middle region, an uninsulated proximal region, and an uninsulated distal region.

* * * * *